(12) United States Patent
Gessert et al.

(10) Patent No.: US 8,893,541 B2
(45) Date of Patent: Nov. 25, 2014

(54) TESTING OF ACOUSTIC IMAGING SYSTEMS OR PROBES

(75) Inventors: James Gessert, Loveland, CO (US); G. Wayne Moore, Lyons, CO (US)

(73) Assignee: Acertara Acoustic Laboratories LLC, Longmont, CO (US)

( * ) Notice: Subject to any disclaimer, the term of this patent is extended or adjusted under 35 U.S.C. 154(b) by 152 days.

(21) Appl. No.: 13/555,899

(22) Filed: Jul. 23, 2012

(65) Prior Publication Data

US 2014/0020469 A1 Jan. 23, 2014

(51) Int. Cl.
*G01N 29/24* (2006.01)
*G01N 29/36* (2006.01)

(52) U.S. Cl.
USPC ............................................. 73/1.82; 73/618

(58) Field of Classification Search
USPC ............... 73/25–26, 571, 599, 603, 618–626, 73/645–648, 632–634, 644; 600/437–447
See application file for complete search history.

(56) References Cited

U.S. PATENT DOCUMENTS

| | | | |
|---|---|---|---|
| 4,651,567 A * | 3/1987 | Sandhu | 73/603 |
| 4,722,346 A * | 2/1988 | Chen | 600/459 |
| 4,936,138 A * | 6/1990 | Cushman et al. | 73/146 |
| 6,035,696 A * | 3/2000 | Kiefer et al. | 73/1.82 |
| 6,122,968 A * | 9/2000 | Vandervalk | 73/642 |
| 6,552,841 B1 * | 4/2003 | Lasser et al. | 359/305 |
| RE40,456 E * | 8/2008 | Bates | 367/7 |
| 2003/0158479 A1 * | 8/2003 | Li et al. | 600/437 |
| 2007/0038096 A1 * | 2/2007 | Seip et al. | 600/439 |
| 2012/0165665 A1 * | 6/2012 | Sandstrom et al. | 600/437 |
| 2012/0184849 A1 * | 7/2012 | Sandstrom et al. | 600/438 |

* cited by examiner

*Primary Examiner* — Peter Macchiarolo
*Assistant Examiner* — Anthony W Megna Fuentes
(74) *Attorney, Agent, or Firm* — Marsh Fischmann & Breyfogle LLP; Jonathon A. Szumny

(57) ABSTRACT

Appliances and methods are disclosed for testing operation of an acoustic device that generates beams of acoustic energy. An imaging array generates electrical signals in response to impinging receipt of acoustic energy. An acoustic-energy direction system is disposed to focus acoustic energy onto the imaging array. A controller is electrically coupled with the acoustic device and with the imaging array. The controller has instructions to generate an image on a display from electrical signals received by the controller from the imaging array. The electrical signals are received by the controller in response to generation of a beam of acoustic energy by the acoustic device. The beam of acoustic energy is directed towards the acoustic-energy direction system. The image provides a representation of the generated beam of acoustic energy.

29 Claims, 7 Drawing Sheets

TESTING OF ACOUSTIC IMAGING SYSTEMS OR PROBES

BACKGROUND OF THE INVENTION

This application relates generally to acoustic systems and probes. More specifically, this application relates to methods and appliances for testing acoustic system and/or probes.

Acoustic imaging is an important technique that may be used at different acoustic frequencies for varied applications that range from medical imaging to nondestructive testing of structures. The techniques generally rely on the fact that different structures have different acoustic impedances, allowing characterization of structures and their interfaces from information embodied by the different scattering patterns that result. While most applications use radiation reflected from structures, some techniques make use of information in transmitted patterns also.

Transmission of acoustic radiation towards a target and receipt of the scattered radiation may be managed by a modern acoustic-imaging system, which may take a variety of forms. For example, many modern systems are based on multiple-element array transducers that may have linear, curved-linear, phased-array or similar characteristics, and which may be embodied in an acoustic probe. Summing the contributions of the multiple transducer elements comprised by a transducer array allows images to be formed. The failure of a small number of elements in a given array, or a few defective receive channels in the acoustic system itself, may not be readily perceptible to users because of the averaging effect of summing many elements to form an acoustic beam. But the failure of even a small number of elements or receive channels can significantly degrade the performance of acoustic imaging systems, notably in certain modes of operation like those known as "Doppler" or "near-field" imaging modes.

While appliances have previously been developed to test acoustic systems and probes, they have been relatively complex, based on the direct electrical connection to probe elements or system channels. The development of two-dimensional "matrix array" probe technology has made the necessary reverse engineering of even a small number of probe and system models to support direct electrical-connection-based testing complex and expensive. Other solutions use an acoustic sensor to detect transmit energy emanating from a probe and to inject signals back into the ultrasound system for detection and display. Such solutions use a single sensor designed to sense elements in linear arrays, providing only a "signal" or "no signal" status relative to transmitted energy and require operator skill to scan a linear array probe for missing or nonfunctional elements.

There is thus a need in the art for convenient, inexpensive, and easy-to-use methods and appliances for evaluating ultrasonic probes and systems, both for acoustic power output as well as for other issues such as failed elements or channels, particularly to evaluate two-dimensional array probes and systems.

SUMMARY

Embodiments of the invention provide appliances for testing operation of an acoustic device that generates beams of acoustic energy. Such appliances may comprise an imaging array, an acoustic-energy direction system, and a controller. The imaging array generates electrical signals in response to impinging receipt of acoustic energy. The acoustic-energy direction system is disposed to focus acoustic energy onto the imaging array. The controller is electrically coupled with the acoustic device and with the imaging array. The controller has instructions to generate an image on a display from electrical signals received by the controller from the imaging array. The electrical signals are received by the controller in response to generation of a beam of acoustic energy by the acoustic device. The beam of acoustic energy is directed towards the acoustic-energy direction system. The image provides a representation of the generated beam of acoustic energy.

The acoustic-energy direction system may comprise an acoustic lens.

In some embodiments, the acoustic device generates beams of acoustic energy in a scanning pattern. The controller comprises instructions to capture a subset of the beams of energy defined by the scanning pattern, with the image providing a representation of the captured subset of the beams of energy defined by the scanning pattern. In one embodiment, the subset of the beams comprises a peak pulse of the scanning pattern.

The imaging array and the acoustic-energy direction system may be disposed within an acoustically transmissive medium confined within a housing body, with the testing appliance further comprising an acoustic couplant coupled with the housing body. In some embodiments, the testing appliance may further comprise an acoustic standoff coupled with the acoustic couplant external to the housing body. In one such embodiment, the acoustic standoff comprises a second housing body filled with a second acoustically transmissive medium. In other embodiments. the testing appliance further comprises a volume of tissue-equivalent material coupled with the acoustic standoff.

An acoustic source transducer may be provided to generate an acoustic signal to be injected into the acoustic device. For example, an acoustic beamsplitter may be disposed to direct the generated acoustic signal into the acoustic device. In other instances, the acoustic source transducer may be disposed on a moveable stage.

The information collected by the imaging devices enables a number of diagnostic determinations. In one embodiment, for example, the controller has instructions to determine a total power of the generated beam of acoustic energy from the electrical signals. In other embodiments, the controller has instructions to determine an acoustic dosimetry provided by the generated beam, to calculate a thermal index for the generated beam, and/or to calculate a mechanical index for the generated beam.

In methods of the invention, operation of an acoustic device that generates beams of acoustic energy is tested. A beam of acoustic energy generated by the acoustic device is directed to an acoustic-energy direction system disposed to focus the acoustic energy onto an imaging array. Electrical signals generated by the imaging array in response to impinging receipt of acoustic energy are received. An image is generated on a display from the electrical signals. The image provides a representation of the generated beam of acoustic energy.

In some embodiments, the acoustic device is moved relative to the imaging array.

The acoustic-energy direction system may comprise an acoustic lens.

In some instances, the acoustic energy generated by the acoustic device comprises beams of acoustic energy in a scanning pattern, with electrical signals corresponding to a subset of the beams of acoustic energy defined by the scattering pattern being received. The image then provides a representation of the captured subset of the beams of acoustic energy defined by the scattering pattern. In one embodiment, the subset of the beams comprises a peak pulse of the scanning pattern.

The generated beam of energy may be directed to the acoustic-energy direction system through an acoustically transmissive medium confined within a housing body that contains the imaging array and the acoustic-energy direction system. In some instances, the generated beam of energy is directed through an acoustic standoff coupled with the housing body. The acoustic standoff may comprise a second housing body filled with a second acoustically transmissive medium. In other instances, the generated beam may be directed through a volume of tissue-equivalent material coupled with the acoustic standoff.

Embodiments also enable the injection of an acoustic signal into the acoustic device, as well as determining various characters that include an acoustic dosimetry provided by the generated beam, a thermal index for the generated beam, and/or a mechanical index for the generated beam.

BRIEF DESCRIPTION OF THE DRAWINGS

A further understanding of the nature and advantages of the present invention may be realized by reference to the remaining portions of the specification and the drawings, wherein like reference labels are used through the several drawings to refer to similar components. In some instances, reference labels are followed with a hyphenated sublabel; reference to only the primary portion of the label is intended to refer collectively to all reference labels that have the same primary label but different sublabels.

DETAILED DESCRIPTION OF EXEMPLARY EMBODIMENTS

Figure 1:
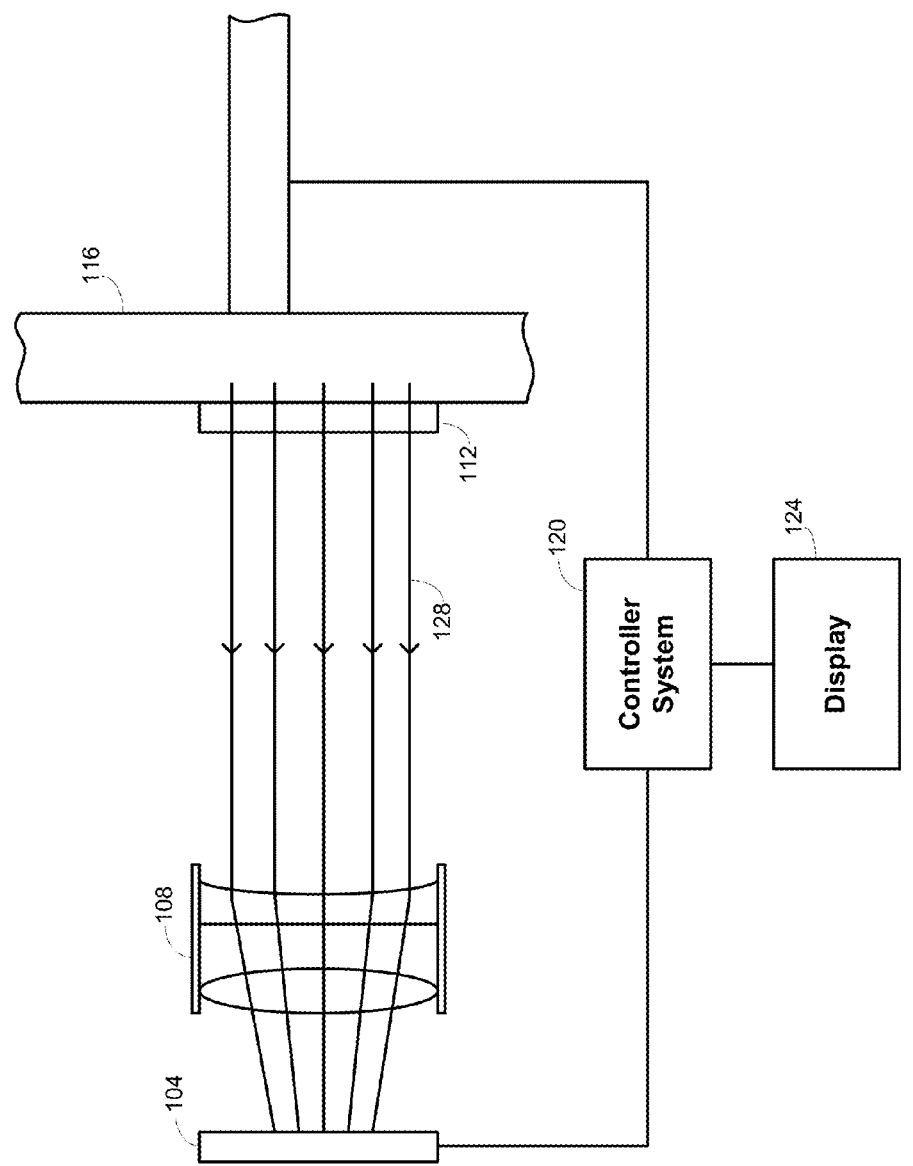
FIG. 1 is a schematic drawing that provides an overview of embodiment appliances of the invention for testing acoustic systems or probes.

Embodiments of the invention provide methods and appliances for testing acoustic systems and/or probes. Such acoustic systems and probes are sometimes referred to collectively herein as "acoustic devices." While much of the description below makes use of specific examples in discussing various aspects of the invention, such examples are intended merely for illustrative purposes; the invention is not intended to be limited by any operational characteristics used by the tested probe or system, such as the operational frequency of the tested acoustic device. As illustrated in further detail below, each of the acoustic probes and systems that may be tested with embodiments of the invention includes a plurality of "transducer elements," which refers to elements adapted to transmit acoustic radiation and/or to receive acoustic radiation. While such elements are referred to generically herein as "transducer elements," they may be distinguished at times according to their functions by describing them as "receiver elements" or "transmitter elements."

Embodiments of the invention provide an appliance that senses and displays the energy distribution over a contact surface of an acoustic probe. It further provides a calibrated measurement appliance capable of integrating the total acoustic output of the acoustic system and thereby determining the acoustic power. In some implementations, the appliance is further capable of injecting various acoustic signals back into the acoustic system via the probe aperture for detection and display. A two-dimensional image of the acoustically active aperture of the probe with the corresponding energy level provides a convenient operator interface that may be used in establishing an acoustic signature for a given probe type. In some instances, such an image may be color coded and may be presented with an integrated total power measurement. It will be appreciated by those of skill in the art that the resultant information may find utility in verifying various output parameters such as the mechanical index ("MI"), the thermal index ("TI"), and the soft-tissue thermal index ("TIS").

The testing appliance is generally configured to have adequate resolution to detect missing elements from a variety of different probe configurations, including one-dimensional and two-dimensional matrix-array probes. Because some current two-dimensional matrix-array probes have nearly 10,000 elements and future probes may have in excess of that number of elements, some implementations of the invention use a smaller sensor that has adequate resolution but not large enough to cover the complete array. The combination of such a sensor with position-sensing using any of a variety of techniques allows an operator to move the sensor over the surface of the probe being tested and thereby accumulate an imaging showing the acoustic energy distribution emanating from the probe. Examples of suitable sensor options include a mechanical linear-motion sensor attached to the probe or an optical position sensor.

In one example, the acoustic sensor is configured as a line array as long as the shortest dimension of the array to be tested. With such a configuration, the probe being tested may be swiped across the linear sensor with a resultant two-dimensional image assembled using the linear position sensor to track the motion of the probe to spatially register the detected acoustic information. In another example, the line array is expanded from element wide to two, three or more elements wide. This may improve signal-to-noise values and provide for additional image registration. In a further example, a small two-dimensional sensor array is scanned over the surface of the probe with motion patterns such as a raster pattern to produce a complete two-dimensional image of the probe's acoustic output energy. This approach may further allow the use of the detected acoustic information to collect and to spatially register images to form an image covering the full aperture of the probe's surface. Merely by way of illustration, a 12×12 mm$^2$ sensor allows scanning of almost all current ultrasound probes with a single swipe, although differently sized sensors may be used with other existing or future probes.

An overview of the functionality of testing appliances according to embodiments of the invention is provide with FIG. 1. In this drawing, a probe head 116 provides acoustic radiation denoted generally by rays 128. The radiation is detected by an imaging array 104 after being directed using an acoustic-energy direction system 108 that may comprise such elements as acoustic lenses, acoustic mirrors, and the like. Generally, the acoustic-energy direction system 108 may comprise elements configured for gross or precise direction and/or shaping of the acoustic radiation 128 as appropriate for the application. For instance, the probe head 116 may emit unfocused acoustic radiation that is directed to the imaging array 104 by the acoustic-energy direction system 108. The acoustic radiation 128 is propagated in a medium suitable for the propagation of acoustic radiation, such as water, with a couplant 112 being provided to couple the radiation emitted by the probe head 116 to the medium.

Any number of acoustic elements may be comprised by the acoustic-energy direction system 108, particularly including multiple-acoustic-lens arrangements. Such systems may be configured according to known acoustic principles to provide dual-lens, triple-lens, and other arrangements. For example, the acoustic magnification provided by a lens is determined by the focal length f of the lens as related to the object distance $d_o$ and image distance $d_i$ by the lens equation:

$$\frac{1}{d_o} + \frac{1}{d_i} = \frac{1}{f}.$$

Since the magnification M provided by a lens is the ratio of object to image distance, i.e. $M \equiv d_o/d_i$, variations in focal length result in variations in the magnification. A zoom lens arrangement provides certain advantageous characteristics and may be implemented in a variety of different ways. For example, a three-lens system having a first positive lens, a second negative lens, and a third positive lens may be used to implement a zoom system. In a particular embodiment, the first and second lenses have equal (but opposite) power so that with their focal lengths being denoted respectively as $f_1$ and $f_2$, the range of effective focal length $f^{(eff)}$ is given by $$\frac{f_1 f_2}{f_1 + f_2} \le f^{(eff)} \le \frac{2 f_1 f_2}{f_1 + 2 f_2}.$$

Maximal effective focal length is achieved with a substantially zero separation between the two lenses, decreasing with separation until the separation approaches $f_1$. The third lens in the arrangement uses the virtual image formed by the first two lenses as an object, collimating the diverging rays to form an image on the imaging array 104. Axial movement of the central negative lens thus varies the power of the system, providing a zoom arrangement. Methods known in the art may be used to vary the position of the central negative lens, and it will be understood that a variety of other lens configurations may be used in providing zoom functionality.

A controller system 120 may be used to coordinate the operation of the probe being tested with the imaging array 104, particularly to provide triggering functions described in greater detail below. Images collected by the imaging array 104 may accordingly be displayed on a display 124 for evaluation by an operator.

Figure 2:
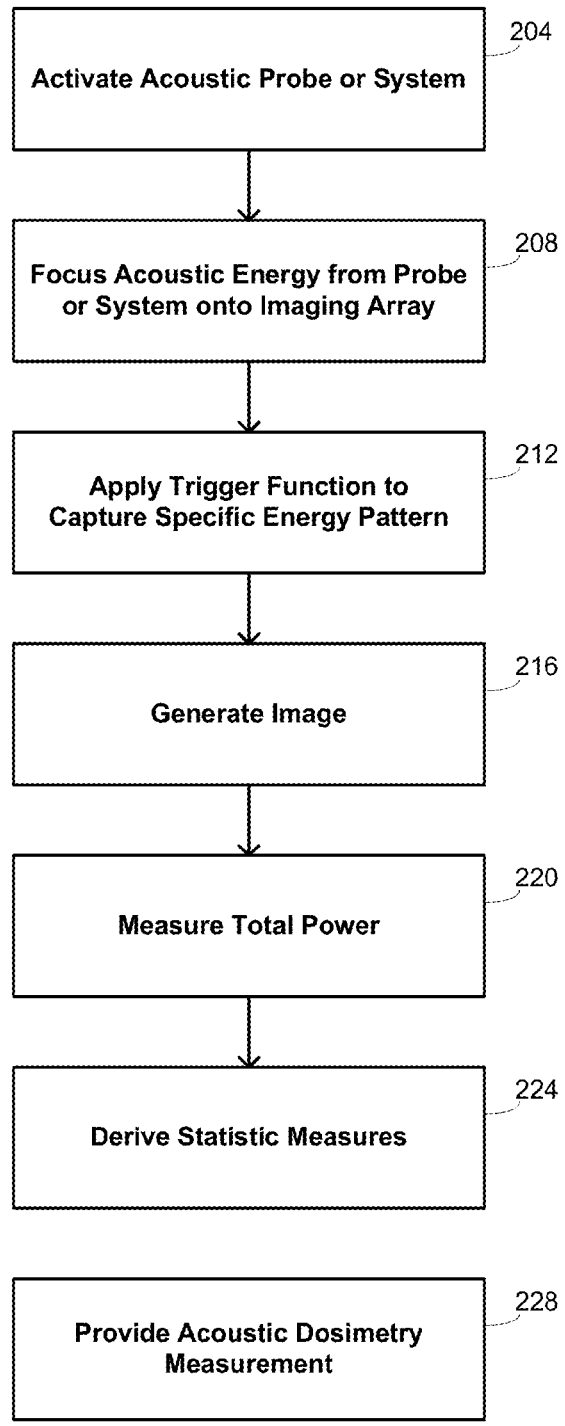
FIG. 2 is a flow diagram that summarizes embodiment methods of the invention for testing acoustic systems or probes.

FIG. 2 provides a flow diagram that summarizes methods for testing acoustic probes and/or systems in accordance with embodiments of the invention and that may use appliances like those illustrated with FIG. 1. At block 204, the acoustic probe or system 116 is activated, coupling the radiation generated by a set of transducers in the acoustic propagation medium with the couplant 112. The acoustic-energy direction system 108 directs the radiation 128 onto the imaging array 104 at block 208.

At block 212, a triggering function is applied to capture a specific energy pattern. Acoustic imaging systems generally use complex scanning patterns so that evaluation of its operation can be improved by consistent selection of a portion of the scanning pattern. In one embodiment, the largest pulse for a given probe is selected by capturing the peak pulse from successive image frames. This prevents mixing transducer pulses that may be pointed in various directions, and improves the calibration of such quantities as total power output, mechanical index, thermal index, soft-tissue thermal index, and the like. Triggering is implemented with the controller system 120 by causing the imaging array 104 to capture an image at appropriate times in accordance with the selection.

Accordingly, at block 216, the image is generated for display on the display 124. As explained above, defects in individual transducer elements may be readily detected by gaps in the resulting image.

At block 220, the total power may be measured and included as part of the display. The total power measurement provides a ready and convenient basis for the calibration of individual probes and systems. Such calibration is difficult with prior-art methodologies, particularly since probes are prone to changing their overall power output over the typical lifetime of a probe. In medical environments, excessive output acoustic levels may increase tissue heating and cause possible injuries that are not otherwise easily detected. The ability of the invention to observe exactly what is emitted from the probe (and therefore into a patient when the probe is used medically) provides a particularly valuable measure.

In addition to determining the total power from the acoustic radiation received at the imaging array 104, certain statistical measures may be derived at block 224. For example, the mechanical index is defined as the quotient of the peak negative pressure $P_-$ and the square root of frequency $f_0$:

$$MI = \frac{P_-}{\sqrt{f_0}}.$$

The mechanical index provides an indicator of possible nonthermal bioeffects from acoustic insonification of biological tissue, such as may result from cavitation and/or streaming. While existing acoustic systems generally display values for the mechanical index, it is known that the accuracy is highly variant; the value displayed by the system may differ from the actual value by 50% or more. The ability for accurate determination of the mechanical index thus provides a valuable source of information. Even in nonmedical contexts, the value of the mechanical index may be relevant in defining human-safety protocols in use of acoustic probes.

The thermal index is defined as the ratio of the power used to the power required to produce a temperature rise of 1° C. It thus provides a measure of thermal effects on biological tissue resulting from insonification. Three sub indices provide specific measures in soft tissue ("TIS"), in bone ("TIB"), and in the cranium ("TIC"). Again, such measures are known to be determined with highly variable accuracy by the acoustic systems themselves so that an ability for direct determination of their values allows more reliable decisions to be made about the use of specific, individual probes in both medical and nonmedical contexts.

The general purpose of the TI is to translate the relative acoustic output power of an acoustic system or probe into a quantity that correlates with models for tissue heating due to acoustic exposure. As the output power of an acoustic system or probe increases, so does the TI. The temperature rise in vivo is also significantly influenced by how the acoustic energy propagates through the tissue. Using highly focused model of operation with stationary acoustic beams such as "spectral Doppler" (e.g., pulsed wave and continuous wave)

and TM-mode focus the acoustic energy into a smaller area (i.e., high time average acoustic intensity) and in the case of continuous-wave Doppler, results in higher localized temperature increases. In non-scanning modes, the location of the maximum temperature rise varies as a function of the size of the active aperture of the probe. For example, with a smaller aperture, the tissue closer to the energy source is the area of highest temperature rise.

Conversely, scanning modes of operation such as B-mode imaging disperse the acoustic power over a wider area, known as the field of view, resulting is less-localized tissue heating at increased depths. In vivo acoustic intensity also decreases as a function of depth because of attenuation of acoustic energy (i.e., tissue attenuation coefficient). In addition to acoustic intensity, the resulting temperature rise also depends on the rate at which the energy is converted into heat in the tissue (i.e., tissue absorption coefficient), the diffusion of the heat in the tissue (i.e., thermal conductivity), and the rate at which the heat is removed by blood flow in the tissue (i.e., blood perfusion). The tissue location that receives the maximum acoustic exposure for the longest time, i.e. acoustic dose, is the point of probe contact at the tissue contact surface.

It is widely held that the TI gives a relative indication of the potential for temperature increase at a specific point along the acoustic beam and therefore that the TI provides a relative indication of exposure conditions that are more likely than others to produce thermal effects. But the duration of exposure is known to be a critical factor in determining the likelihood of inducing a thermal effect, with the risk of thermal damage increasing exponentially with exposure time. The values of TI displayed on current ultrasound system monitors do not include any dependence on exposure time. As a result, a longer exposure at a lower TI might be more of a risk to a patient than a shorter exposure at a higher TI. Since the system-displayed values do not inform the operator of risk based on exposure duration, the TI value is, at best, a weak indication of potential patient harm from excessive thermal load.

The dimensionless TI and MI values displayed on contemporary ultrasound system monitors are not measures of the actual energy present at the aperture of a specific probe on a specific system; they are rather a statistical composite of a population of in-kind probes on in-kind systems and may not provide an adequate measure of exposure risk in newer modalities. Embodiments of the invention are able to better respond to the growing complexity of systems, probes, modalities, clinical applications, and concerns about patient safety by directly visualizing and measuring the energy present at the probe aperture (tissue contact surface) and providing an acoustic dosimetry measurement as indicated at block 228.

Acoustic sensors in the imaging array 104 may be made of a variety of different materials in different embodiments, including both polyvinylidene fluoride ("PVDF") and ceramics. PVDF is both flexible and inexpensive, but is less efficient than the ceramic lead zirconate titanate ("PZT"). While PVDF is a relatively poor transmitter, this is not a significant barrier to its use in embodiments of the invention because output levels equivalent to returning tissue echoes are also very low and readily sensed by medical ultrasound systems.

Figure 3A:
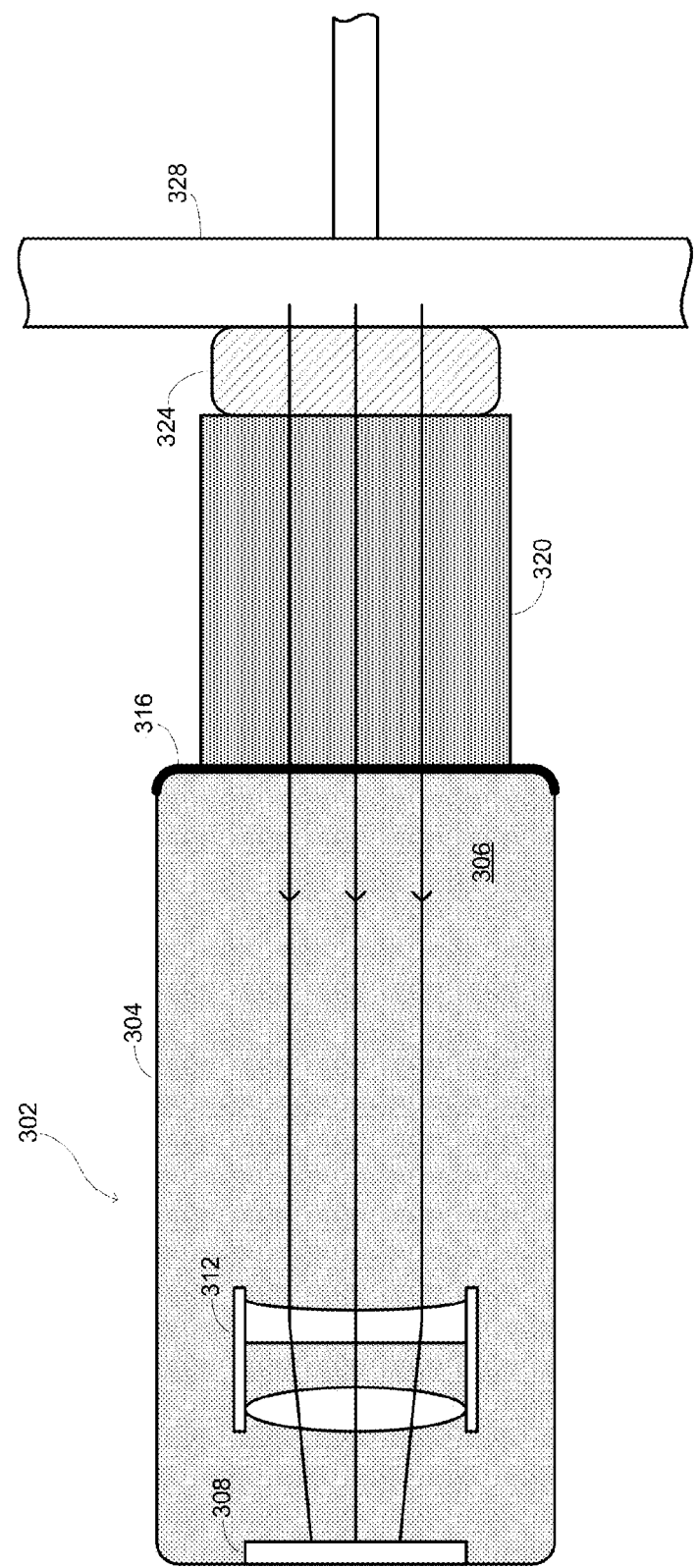
FIGS. 3A and 3B provide illustrations of different implementations of the general embodiments of FIG. 1.
Figure 3B:
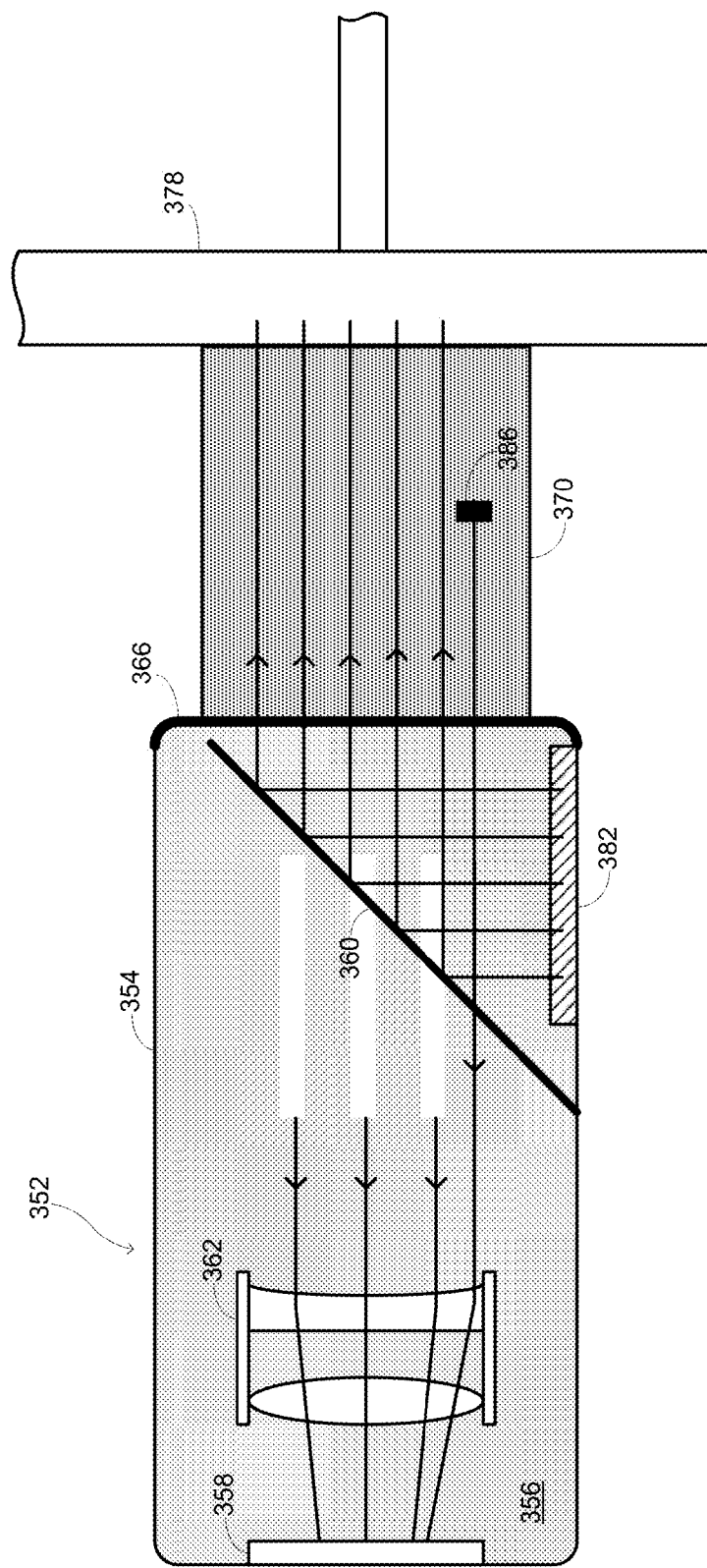

Specific implementations of the testing appliances are illustrated in FIGS. 3A and 3B. While the specific features shown in those drawings may be implemented separately or in combination, they are shown separately in the drawings for ease of illustration. In both cases, a portion of the structures are embodied in an acoustic camera. In FIG. 3A, for example, the acoustic camera is denoted generically by reference number 302 and comprises a body 304 within which the imaging array 308 and acoustic-energy direction system 312 are disposed within an acoustically transmissive medium 306. A couplant 316 allows acoustic energy to be coupled between the exterior of the housing 304 and the acoustically transmissive medium 306, and may be made of a material such as silicone rubber, urethane, or latex.

In some embodiments, depending on the specific configuration of the elements, it is possible to couple acoustic radiation emanating from a probe directly to the couplant 316. But in other instances, geometrical considerations indicate that electrical interference may result from such a direct coupling because of the proximity of the surface aperture of the acoustic probe 328. Accordingly, an acoustic standoff 320 may be used to provide a physical path that isolates the acoustic signal from the electrical signal by the time delay between them. Such an acoustic standoff 320 may be implemented in a variety of ways. In the illustrated embodiment, the acoustic standoff comprises a body filled with an acoustically transmissive medium, taking advantage of the focal imaging approach used by the acoustic camera 302 and described above. The acoustic-energy direction system 312 focuses the energy at a specific distance from the sensor, and may be set to provide an image of the energy as it leaves the probe 328. In other embodiments, the acoustic standoff is provided as a thin element to avoid excessive divergence of the acoustic signal from the array elements over the additional path distance.

In addition to the acoustic standoff 320, FIG. 3A illustrates the incorporation of a tissue-equivalent material 324 disposed between the probe 328 and other elements of the appliance. Such tissue-equivalent material 324 may serve multiple functions, particularly for the testing of probes intended for medical applications. In such medical applications, there are two principal sources of tissue heating—the direct effect of acoustic energy propagated into tissue and also conductive heating that results from the conversion efficiency of piezoelectric transducers. The inclusion of tissue-equivalent material both absorbs acoustic energy and allows models to matched for combining instruments to measure power and surface-temperature rises. This enables the use even of acoustic cameras 302 designed for the detection of highly attenuative signals despite the fact that the acoustic signals generated by acoustic probes are only weakly attenuated. The reduction in the signal level allows optimization of the dynamic range of the sensor. There are a variety of materials that may be used for the tissue-equivalent material 324, including agar, silicone, polyvinyl alcohol gel ("PVA"), and polyacrylamide gel ("PAA"), among others.

FIG. 3B illustrates another embodiment in which a portion of the structures are embodied within an acoustic camera denoted generically in the drawing by reference number 352, with a body 354 containing the imaging array 358 and acoustic-energy direction system 362 within an acoustically transmissive medium 356. Similar to the embodiment of FIG. 3A, this embodiment includes a couplant 366 and may include an acoustic standoff 370 implemented with any of the variations described in connection with FIG. 3A. In addition, though, this embodiment includes an acoustic source transducer 382. While shown implemented as part of the acoustic camera 352 by having it disposed within the camera body 354, this is not a requirement of the invention and other possible positions may be used.

The acoustic source transducer 382 may be used to inject acoustic signals back into the probe 378. When incorporated as part of the acoustic camera 352, an acoustic beam splitter 360 may be included to manage direction of the source acoustic signals injected back into the probe 378 and the received acoustic signals generated by the probe 378. The beam generated by the acoustic source transducer 382 impacts the acoustic beam splitter 360, where the beam is split such that any desired fraction of the beam is reflected from the beam splitter 360 and out through the couplant 366.

The acoustic beam splitter 360 may be of any of a variety of types, including those composed of a material that has an acoustic-impedance mismatch with the acoustically transmissive medium 356. Because of the acoustic-impedance mismatch, the material of the acoustic beam splitter 360 reflects a portion of the acoustic beam transversely while transmitting a portion of the beam so that it propagates axially. The thickness of the material of the acoustic beam splitter 360 can advantageously be selected such that the thickness is greater than half a wavelength of the source acoustic beam to ensure a sufficient acoustic mismatch, but different material thicknesses may be used in different embodiments. In one exemplary embodiment, the thickness of the acoustic beam splitter 360 is selected such that a ratio of the transverse reflected beam to the axial transmitted beam is approximately 50%, although other ratios may be used in different embodiments. Examples of materials suitable for use for the acoustic beam splitter 360 include thin sheets of glass or metal such as aluminum or steel, but other materials may also be used.

FIG. 3B also shows the inclusion of a second acoustic source transducer 386 that may aid in accurate determinations of the mechanical index for the probe 378. The second acoustic source transducer 386 may advantageously be deployed on a moveable stage (not shown) adapted to be moved manually or with a motorized mechanism. Such a motorized mechanism may be controlled by the controller system 120 described in connection with FIG. 1. The ability to position the second acoustic source transducer 386 enables the determination of the peak negative pressure P_at a known depth, permitting accurate determination of the mechanical index. In one embodiment, the second acoustic source transducer 386 comprises a single-sheet PVDF transducer placed about 6 cm from the probe face, although different types of transducers and different geometrical arrangements may be used in different embodiments.

Signals from the second acoustic source transducer 386 can be used to identify the central beam transmitted to form a two-dimensional image and can also be analyzed to determine the center frequency of the transmitted energy. The appliance of the invention may thus be used to calculate a TI value—or a TIS, TIB, or TIC value—that can be compared with the value displayed be the acoustic system, enabling a calibration of the display values. In addition, setting the acoustic system to focus at the distance of the second acoustic source transducer 386 provides a pressure signal that can be used to calculate an estimate of the current MI value that is also displayed by the acoustic system.

Figure 4:
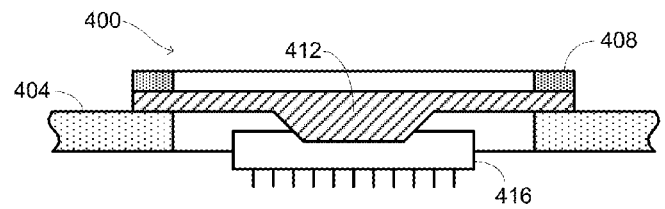
FIG. 4 illustrates a structure of an array interface for coupling acoustic energy onto an imaging array that may be used in some embodiments.

The acoustic beam focused by the acoustic-energy direction system in any of these embodiments may sometimes be coupled onto the imaging array through an array interface like that shown in FIG. 4. Such an array interface is not required in all embodiments of the invention but advantageously prevents the acoustically transmissive medium within the housing of the acoustic camera from contacting the imaging array. The imaging array is denoted generically by reference number 416 in FIG. 4 and corresponds to imaging array 104, 308, or 358 in FIG. 1, 3A, or 3B. The array interface 400 comprises a diaphragm 412 having a truncated conical segment and a retainer ring 408. The diaphragm 412 is sealed to a backplate 404 using the retainer ring 408. The diaphragm 412 comprises an acoustically transmissive material such as polyurethane, allowing the coupling of acoustic energy from the acoustically transmissive medium onto the imaging array 416 while preventing the acoustically transmissive medium from contacting the imaging array 416.

Advantageously, embodiments of the invention are not limited by the particular structure of the acoustic probe or system being tested, are not limited by the frequency characteristics of the acoustic probe or system being tested, and do not require the use of adapters to accommodate different transducer arrangements used by different probes. Examples of different probe structures that may readily be accommodated is provided with FIGS. 5A-5F.

Figure 5A:
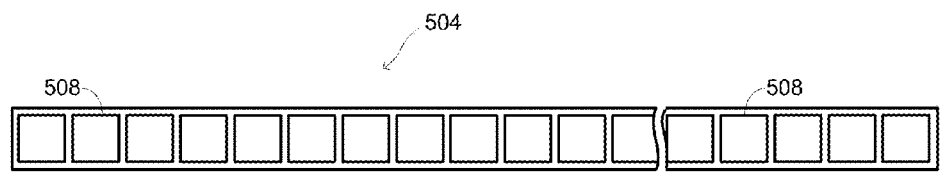
FIGS. 5A-5F provide schematic illustrations of different arrangements for transducer arrays that may be tested using embodiments of the invention.

The array 504 shown in FIG. 5A is a conventional one-dimensional array in which individual acoustic elements 508 are distributed along a length to define the array 504. While the length is shown to be linear in the drawing, the length may more generally be curvilinear, with some acoustic devices having curved distributions of acoustic elements 508.

Figure 5B:
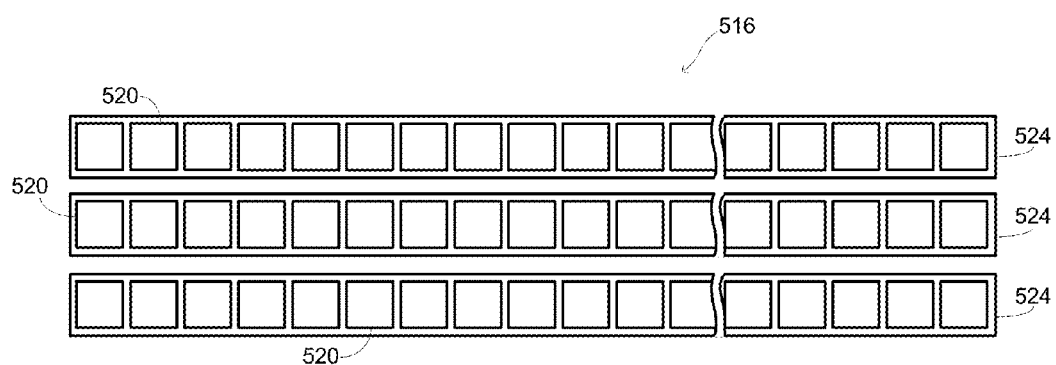

The array 516 shown in FIG. 5B comprises a plurality of one-dimensional arrays 524 spaced along an elevational height. Such an array 516 is sometimes referred to in the art as a "1.5-dimensional array." Acoustic devices having such a 1.5-dimensional array are less successful at near-field imaging, particularly when the elevational height is relatively large. The success of such imaging depends also on the frequency used by the array 516. Accordingly, such arrays 516 sometimes use all of the one-dimensional arrays 524 when imaging the far field, but use only a smaller subset of the one-dimensional arrays 524—perhaps only a single one-dimensional array 512—when imaging the near field.

Figure 5C:
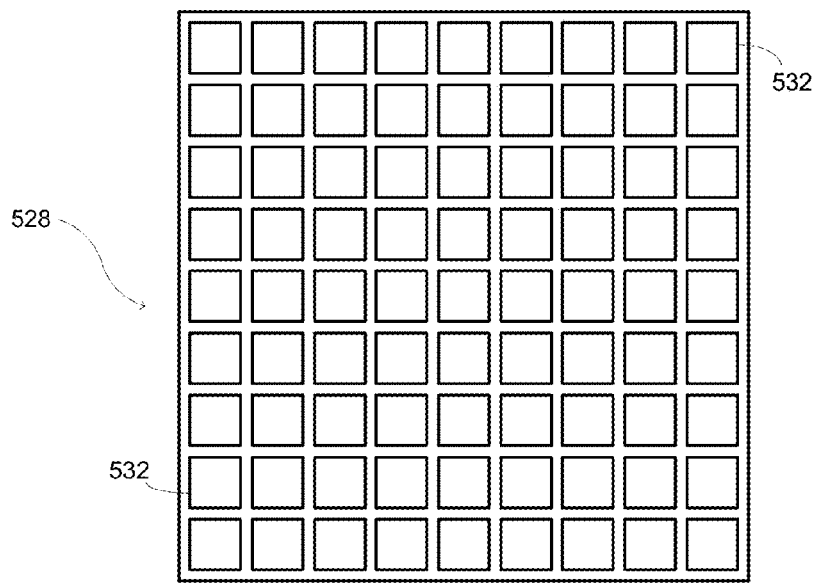

The array 528 shown in FIG. 5C is a two-dimensional matrix array, with the individual transducers 532 distributed in a regular pattern. Such probes may have an active area divided in two dimensions in different elements, and allow the acoustic beam to be driven in three dimensions by combining electronic focusing and deflection.

Figure 5D:
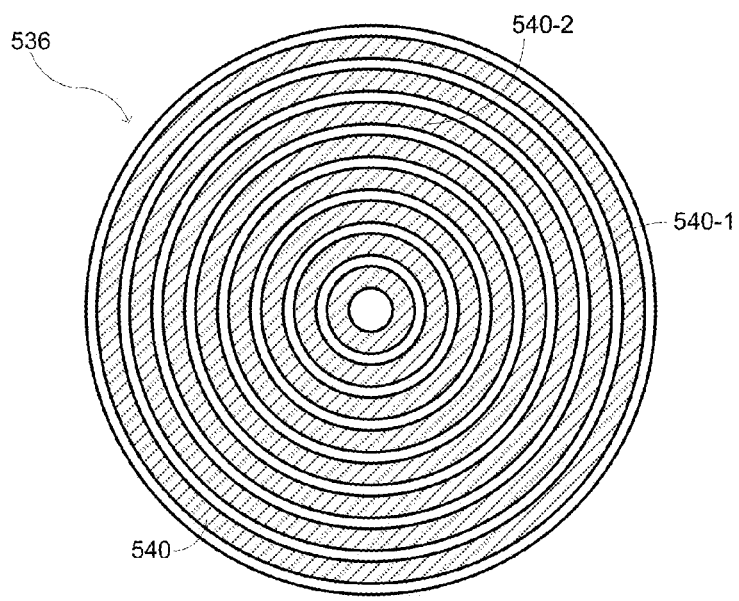

The array 536 shown in FIG. 5D is an annular array made up of a set of concentric rings 540. They allow the beam to be focused to different depths along an axis. While the structure illustrated is one in which the radial width of each ring 540 is constant, other structures use a different width for each ring 540 so that the surface area of the rings 540 is constant.

Figure 5E:
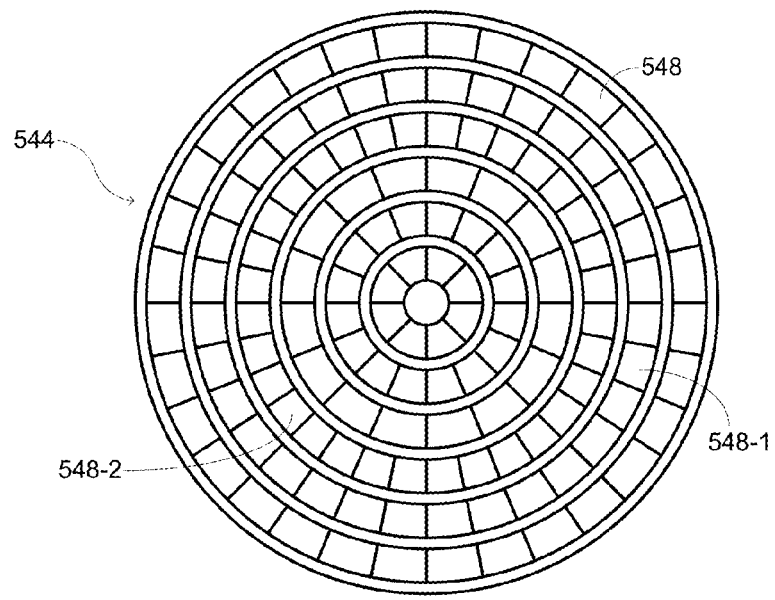

Like the array 528 shown in FIG. 5C, the array 544 shown in FIG. 5E provides an example of a two-dimensional matrix array. The transducers 548 are also arranged in a regular pattern, but as elements arranged in circles. The elements can be directed towards the interior, towards the exterior, or along the axis of symmetry of the circle in different embodiments. When directed along the circle's axis of symmetry, an acoustic mirror may be used to provide the beam with the desired angle of incidence.

Figure 5F:
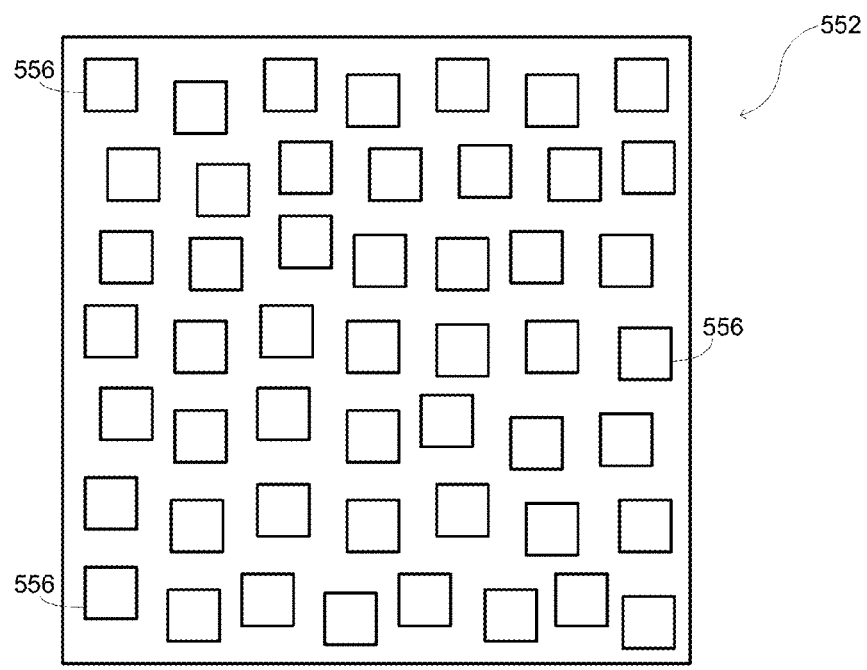

The array 552 shown in FIG. 5F is also a two-dimensional array, but one in which the individual acoustic elements 556 are distributed irregularly. Such an array is referred to in the art as a "sparse array."

While any of the array structures illustrated in FIGS. 5A-5F may be tested in different embodiments of the invention, even by using the same testing appliance, their illustration is not intended to be exhaustive. Still other array structures not explicitly illustrated may be tested using the methods and appliances described herein.

Having described several embodiments, it will be recognized by those of skill in the art that various modifications, alternative constructions, and equivalents may be used without departing from the spirit of the invention. Accordingly, the above description should not be taken as limiting the scope of the invention, which is defined in the following claims.

What is claimed:

1. A testing appliance for testing operation of an acoustic device that generates beams of acoustic energy, the testing appliance comprising:
   an imaging array for generating electrical signals in response to impinging receipt of acoustic energy;
   an acoustic-energy direction system disposed to focus acoustic energy generated by a plurality of transducer elements across a surface of the acoustic device onto the imaging array; and
   a controller electrically coupled with the acoustic device and with the imaging array, the controller having instructions to generate an image on a display from electrical signals received by the controller from the imaging array,
   wherein:
      the electrical signals are received by the controller in response to generation of a beam of acoustic energy by the acoustic device;
      the beam of acoustic energy is directed towards the acoustic-energy direction system from the acoustic device; and
      the image provides a representation of a distribution of acoustic energy emanating from the plurality of transducer elements, wherein the image provides an indication of one or more defects of one or more of the plurality of transducer elements.

2. The testing appliance recited in claim 1 wherein the acoustic-energy direction system comprises an acoustic lens.

3. The testing appliance recited in claim 1 wherein:
   the acoustic device generates beams of acoustic energy in a scanning pattern;
   the controller comprises instructions to capture a subset of the beams of energy defined by the scanning pattern; and
   the image provides a representation of the captured subset of the beams of energy defined by the scanning pattern.

4. The testing appliance recited in claim 3 wherein the subset of the beams comprises a peak pulse of the scanning pattern.

5. The testing appliance recited in claim 1 wherein the imaging array and the acoustic-energy direction system are disposed within an acoustically transmissive medium confined within a housing body, the testing appliance further comprising an acoustic couplant coupled with the housing body.

6. The testing appliance recited in claim 5 further comprising an acoustic standoff coupled with the acoustic couplant external to the housing body.

7. The testing appliance recited in claim 6 wherein the acoustic standoff comprises a second housing body filled with a second acoustically transmissive medium.

8. The testing appliance recited in claim 6 further comprising a volume of tissue-equivalent material coupled with the acoustic standoff.

9. The testing appliance recited in claim 1 further comprising an acoustic source transducer that generates an acoustic signal to be injected into the acoustic device.

10. The testing appliance recited in claim 9 further comprising an acoustic beamsplitter disposed to direct the generated acoustic signal into the acoustic device.

11. The testing appliance recited in claim 1 wherein the controller has instructions to determine a total power of the generated beam of acoustic energy from the electrical signals received by the controller from the imaging array, and wherein the total power of the generated beam is presented in the image on the display.

12. The testing appliance recited in claim 1 wherein the controller has instructions to determine an acoustic dosimetry provided by the generated beam.

13. The testing appliance recited in claim 1 wherein the controller has instructions to calculate a thermal index for the generated beam.

14. The testing appliance recited in claim 1 wherein the controller has instructions to calculate a mechanical index for the generated beam.

15. A method for testing operation of an acoustic device that generates beams of acoustic energy, the method comprising:
   directing a beam of acoustic energy generated by a plurality of transducer elements across a surface of the acoustic device to an acoustic-energy direction system disposed to focus the acoustic energy onto an imaging array;
   receiving electrical signals generated by the imaging array in response to impinging receipt of acoustic energy;
   generating an image in a display from the electrical signals, the image providing a representation of a distribution of acoustic energy emanating from the plurality of transducer elements; and detecting defects in one or more of the plurality of transducer elements from the generated image.

16. The method recited in claim 15 further comprising moving the acoustic device relative to the imaging array.

17. The method recited in claim 15 wherein the acoustic-energy direction system comprises an acoustic lens.

18. The method recited in claim 15 wherein:
   the acoustic energy generated by the acoustic device comprises beams of acoustic energy in a scanning pattern;
   receiving electrical signals generated by the imaging array comprising identifying electrical signals corresponding to a subset of the beams of acoustic energy defined by the scattering pattern; and
   the image provides a representation of the captured subset of the beams of acoustic energy defined by the scanning pattern.

19. The method recited in claim 18 wherein the subset of the beams comprises a peak pulse of the scanning pattern.

20. The method recited in claim 15 wherein directing the beam of acoustic energy to the acoustic-energy direction system comprises directing the beam of acoustic energy through an acoustically transmissive medium confined within a housing body that contains the imaging array and the acoustic-energy direction system.

21. The method recited in claim 20 wherein directing the beam of acoustic energy to the acoustic-energy direction system further comprises directing the beam of acoustic energy through an acoustic standoff coupled with the housing body.

22. The method recited in claim 21 wherein the acoustic standoff comprises a second housing body filled with a second acoustically transmissive medium.

23. The method recited in claim 21 wherein directing the beam of acoustic energy to the acoustic-energy direction system further comprises directing the beam of acoustic energy through a volume of tissue-equivalent material coupled with the acoustic standoff.

24. The method recited in claim 15 further comprising injecting an acoustic signal into the acoustic device.

25. The method recited in claim 15 further comprising determining a total power of the generated beam of acoustic energy from the electrical signals, wherein the total power of the generated beam is presented in the image on the display.

26. The method recited in claim 15 further comprising determining an acoustic dosimetry provided by the generated beam.

27. The method recited in claim 15 further comprising determining a thermal index for the generated beam.

28. The method recited in claim 15 further comprising determining a mechanical index for the generated beam.

29. The method recited in claim 15, wherein the detecting defects includes identifying one or more gaps in the generated image.

* * * * *